US00PP15205P2

(12) United States Plant Patent
McNaughton

(10) Patent No.: US PP15,205 P2
(45) Date of Patent: Oct. 5, 2004

(54) ***LAVANDULA* PLANT NAMED 'LAVSTS 11'**

(50) Latin Name: *Lavandula stoechas*
Varietal Denomination: Lavsts 11

(76) Inventor: Virginia McNaughton, Lavender Downs, Lawford Road, West Melton, RD6 Christchurch (NZ)

( * ) Notice: Subject to any disclaimer, the term of this patent is extended or adjusted under 35 U.S.C. 154(b) by 0 days.

(21) Appl. No.: 10/663,852

(22) Filed: Sep. 15, 2003

(51) Int. Cl.[7] ..... A01H 5/00
(52) U.S. Cl. ..... Plt./226
(58) Field of Search ..... Plt./226

*Primary Examiner*—Kent Bell
*Assistant Examiner*—S B McCormick-Ewoldt

(57) ABSTRACT

A new cultivar of *Lavandula* plant named 'Lavsts 11' that is characterized by bushy, semi-open habit, and sterile bracts that change in color from lilac to red-violet, combined with blue-violet corollas. These traits sets it apart from all other existing varieties of Lavandula known to the inventor.

2 Drawing Sheets

Genus: *Lavandula.*
Species: *stoechas.*
Denomination: Lavsts 11.

BACKGROUND OF THE INVENTION

The present invention relates to a new and distinct cultivar of lavender known botanically as *Lavandula stoechas* subsp. *pedunculata* and hereinafter referred to by the cultivar name 'Lavsts 11'. The new invention is a product of pollination between two *Lavandula stoechas* varieties, namely *Lavandula* 'Somerset Mist' (unpatented) and Lavandula 'Gethsemane' (unpatented). The hybrid seedling was selected by the inventor in 1997 in Christchurch, New Zealand. Because of its hybrid nature, it will be known as *Lavandula* 'Lavsts 11'. The female parent of the new hybrid plant 'Lavsts 11' is *Lavandula* 'Somerset Mist' and male parent plant is *Lavandula* 'Gethsemane'. 'Somerset Mist' exhibits bright green bushy foliage and pinkish-green sterile bracts which fade to a dullish purple. 'Gethsemane' exhibits grayish-green foliage and an open habit and flower4s with red-purple sterile bracts suffused with violet along the midrib. Thus Lavsts 11 differs from either parent in respect of foliage (Lavsts 11: mid-green), habit (Lavsts 11: semi-open) and color of sterile bracts (Lavsts 11: different from either, as described herein).

The new lavender plant 'Lavsts 11' is distinct and unique from all other lavenders known to the inventor due to its spikes with rich violet-blue corollas and lilac coloured sterile bracts in combination with mid-green foliage. The sterile bracts change color as they age, to a red-violet giving a two toned appearance to the bush when in flower, making them distinct from all other *Lavandula stoechas* cultivars.

The new invention 'Lavsts 11' was asexually propagated by the inventor in Christchurch, New Zealand in 1997 using soft to semi-hardwood cuttings. Since that time subsequent generations have been determined fixed, stable and true to type.

SUMMARY OF THE INVENTION

The following traits have been repeatedly observed and represent the distinguishing characteristics of the new *Lavandula* cultivar 'Lavsts 11'. These traits in combination distinguish 'Lavsts 11' from all other existing varieties of *Lavandula* known to the inventor. 'Lavsts 11' has not been tested under all possible conditions and phenotypic differences may be observed with variations in environmental, climatic, and cultural conditions, however, without any variance in genotype.

1. *Lavandula* 'Lavsts 11' exhibits a bushy, semi-open habit.
2. *Lavandula* 'Lavsts 11' exhibits sterile bracts that change in color from lilac to red-violet, combined with violet-blue corolla color.
3. *Lavandula* 'Lavsts 11' exhibits short to medium length peduncles.
4. *Lavandula* 'Lavsts 11' exhibits mid-green foliage.

BRIEF DESCRIPTION OF THE DRAWINGS

The accompanying color drawings illustrate the overall appearance of the new cultivar 'Lavsts 11', showing colors as true as it is reasonably possible to obtain in colored reproduction of this type. Colors in the drawings may differ from the color values cited in the detailed botanical description, which accurately describes the actual colors of the new variety 'Lavsts 11'. The drawings are made from 2-year-old plants grown out-of-doors in the ground in Christchurch, New Zealand.

The drawing labeled as FIG. 1 shows the entire plant from a side view perspective, illustrating the plant habit and showing the variation (darkening) of color in the sterile bracts as the flowers age.

Figure 1:
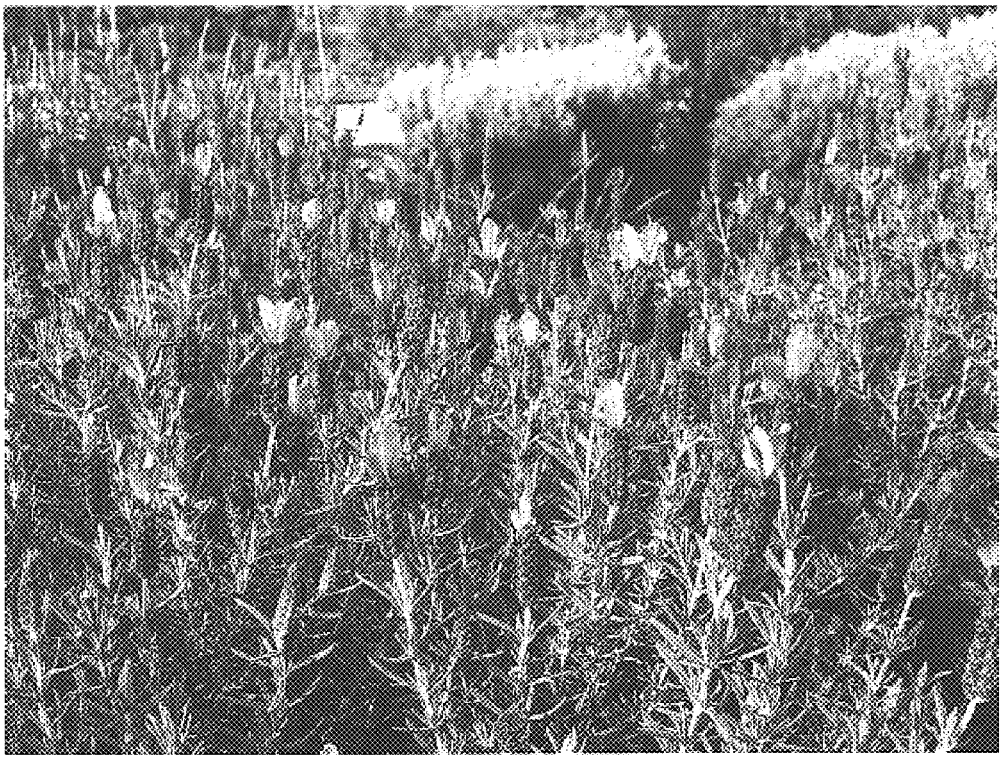
Figure 2:
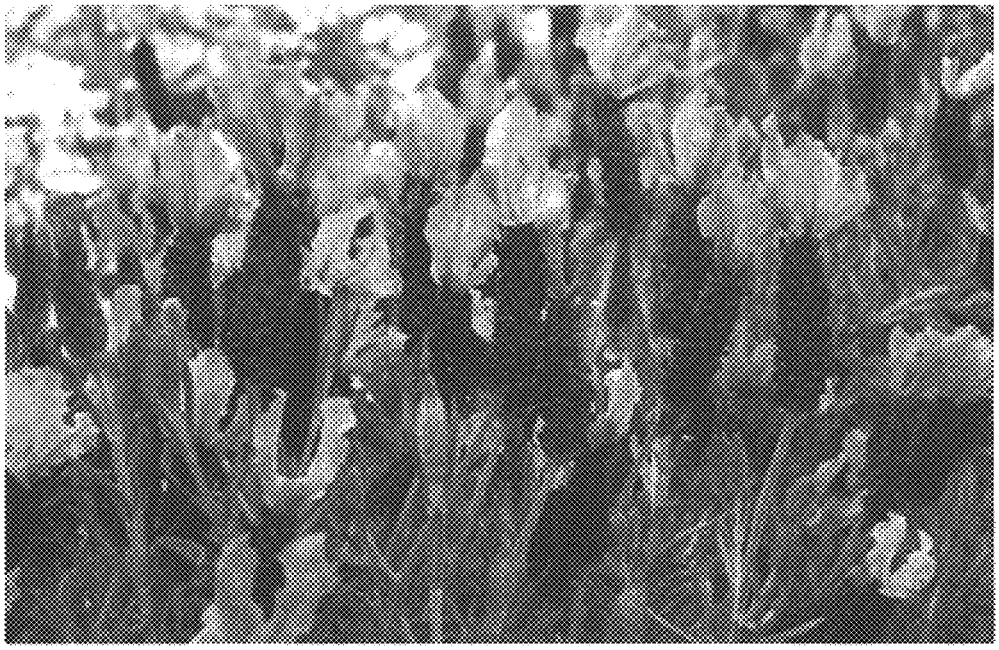

The drawing labeled as FIG. 2 shows a close-up of the flower and sterile bracts at medium age.

Both drawings were made using conventional photographic techniques and although the colors may appear different from the actual colors due to light reflectance, they are as accurate as possible by conventional photography.

BOTANICAL DESCRIPTION OF THE PLANT

The following is a detailed description of the *Lavandula* cultivar named 'Lavsts 11'. Data was collected in West Melton, Christchurch New Zealand from plants grown in the open ground and in dry conditions. Phenotypic differences may be observed with variations in environmental, climatic, and cultural conditions, without however, any difference in genotype. Color determinations are in accordance with The Royal Horticultural Society Colour Chart except where general color terms of ordinary dictionary significance are used. Color determination using The Royal Horticultural Society Colour Chart was conducted using the light box at The New Zealand Plant Variety Rights Office at Lincoln, Canterbury, New Zealand. Please note that the brown, green and violet range in these charts do not have an adequate color range to match that seen in lavender. The growing requirements are similar to the species and no disease problems have been observed.

Botanical classification: *Lavandula* 'Lavsts 11'.
Species: *stoechas*.
Common name: Lavender.
Parentage: 'Lavsts 11' is a hybrid that resulted from the pollination of the following parent plants:
*Female parent plant.*—*Lavandula* 'Somerset Mist'.
*Male parent plant.*—*Lavandula* 'Gethsemane'.
Type: Aromatic perennial shrub.
Use: En mass, ornamental or feature plant in the landscape.
Growth rate: Moderate to vigorous.
Habit: Bushy and semi-open with erect, ascending flower spikes.
Height: 60–70 cm in height.
Spread: 60–70 cm in width.
Hardiness: USDA Zones 5–8.
Disease resistance or susceptibility: No unusual or additional disease resistance or susceptibility compared to other cultivars of the species *Lavandula stoechas*.
Propagation method: Cuttings, tissue culture.
Root system: Fibrous.
Soil: Plant in well-drained soil.
Light levels: Plant in full sun.
Special needs: Prune after flowering to maintain shape and to initiate second flowering period.
Time to initiate roots: 21 to 36 days are needed to develop roots on a cutting.
Time to develop to a one-gallon: 3 months are needed to produce a finished 1-gallon container from a rooted cutting.
Branching habit: Erect, upright and semi-open.
Seasonal interest: Flowers April–July and August.
Stem:
*Shape.*—Square.
*Surface.*—Puberulent.
*Color.*—Older stems 165A (mid-brown). Young stems 138B (olive-green).
*Size.*—1–5 mm in diameter.
Foliage:
*Arrangement.*—Upright stems with whorls of leaves, arranged opposite along stem. A basal pair of leaves subtend each whorl of leaves. Dense arrangement of leaves along stems.
*Leaf division.*—Simple.
*Apices.*—Acute.
*Base.*—Truncate.
*Margins.*—Entire and revolute.
*Leaf shape.*—Linear.
*Color of mature leaves* (*upper*).—189A (mid to dark green).
*Color of mature leaves* (*lower*).—191A (mid green).
*Color of young leaves* (*upper*).—191A (mid green).
*Color of young leaves* (*lower surfaces*).—Too revolute to view.
*Upper and lower surfaces.*—Puberulent on both surfaces.
*Venation.*—Mid vein depressed on upper surface and protruding beneath, side veins noticeable on lower surface with naked eye.
*Internodes.*—0.5–2 cm in length.
*Foliar fragrance.*—Minimal scent of pine and camphor but quite sweet for a *L. stoechas* cultivar. Almost similar to rosemary.
*Petiole.*—Sessile.
*Length.*—Approximately 0.6–3.5 cm in length.
*Width.*—0.5–5 mm in width.
Flower spike:
*Type of inflorescence.*—Terminal spike.
*Size of inflorescence.*—2–5 cm in length and 0.8–1.5 cm in width.
*Shape of inflorescence.*—Mostly cylindric with sterile bracts.
*Peduncles.*—3–5 cm in height and 1–2 mm in width.
*Peduncle hair cover.*—Pubescent to tomentose, the hairs are longer than on the stem.
*Peduncle color.*—138B (olive-green).
*Flower shape.*—Tubular.
*Corolla.*—Two-lipped with upper lip 2-lobed and lower lip 3-lobed.
*Corolla color.*—89A (rich violet-blue).
*Calyx color.*—Green with the upper half suffused with purple. The appendage is purple.
*Calyx surface.*—Puberulent with more hair noticeable close to where the corolla tube emerges.
*Bracteoles.*—None present.
*Fertile bract shape.*—Rhombic-cordate or obovate and acute.
*Fertile bract color.*—Membranous with green veining with an occasional tinge of red-purple.
*Fertile bract hair covering.*—Puberulent with minute hairs around the margin. The hairs are slightly longer and thicker on the margins at the base of the fertile bracts.
*Sterile bract shape.*—Spathulate or oblanceolate.
*Sterile bract margins.*—Moderately undulating.
*Sterile bract length.*—10–20 mm.
*Sterile bract color.*—Opens a soft lilac to mauve-violet shade (84A and 84B both present) and changes to a red-violet (88C) as the sterile bracts age. The color may also be weather dependent.
*Sterile bract number.*—Four.
*Fragrance.*—Camphor.
*Blooming period* (*New Zealand*).—October to February.
*Blooming period* (*U.S.A.*).—April to August.
Reproductive organs:
*Stamens.*—4.
*Stamen length* (*2 posterior*).—2 mm.
*Stamen length* (*2 anterior*).—1 mm.
*Pistil.*—1.
*Pistil length.*—5 mm.
*Pistil diameter.*—Less than 0.25 mm.
*Filament diameter.*—Less than 0.25 mm.
*Filament color.*—Grayish-white.
*Style length.*—5 mm.
*Style color.*—Grayish-white.
*Stigma shape.*—Oval.
*Stigma color.*—Dark gray.
*Ovary shape.*—Slightly oblong to globose.

*Ovary dimensions.*—Too small to match, but approximately 0.5 mm long, and 0.5 mm wide.
*Ovary position.*—Superior.
*Ovary color.*—Green.
*Anther shape.*—Reniform.
*Anther length.*—Less than 0.5 mm.
*Anther color.*—Violet.
*Pollen amount.*—Sparse.
*Pollen color.*—Yellow.

Seed:
*Seeds.*—1–2 per calyx.
*Colour of seeds.*—161A (yellow-brown).
*Length of seeds.*—1–2.5 mm.

I claim:

1. A new and distinct variety of *Lavandula* plant named 'Lavsts 11' as described and illustrated.

* * * * *